United States Patent [19]

Dittmer et al.

[11] Patent Number: 4,741,867
[45] Date of Patent: May 3, 1988

[54] PROCESS FOR THE PREPARATION OF 1-AMINO-2-BROMO-4-HYDROXYAN-THRAQUINONE

[75] Inventors: Helmut Dittmer, Leverkusen; Jürgen Schneider; Hubert Schönhagen, both of Odenthal; Claus Krügermann, Leverkusen, all of Fed. Rep. of Germany

[73] Assignee: Bayer Aktiengesellschaft, Leverkusen, Fed. Rep. of Germany

[21] Appl. No.: 698,988

[22] Filed: Feb. 7, 1985

[30] Foreign Application Priority Data

Apr. 28, 1984 [DE] Fed. Rep. of Germany ....... 3415917

[51] Int. Cl.$^4$ ............................................. C07C 97/26
[52] U.S. Cl. .................................... 260/380; 260/381; 260/687 H; 260/694
[58] Field of Search ................... 260/380, 381, 687 H, 260/694

[56] References Cited

U.S. PATENT DOCUMENTS

| | | | |
|---|---|---|---|
| 2,604,480 | 7/1952 | Seymour et al. | 260/380 |
| 4,197,250 | 4/1980 | Redeker et al. | 260/380 |
| 4,292,247 | 9/1981 | Nishikuri et al. | 260/380 |

FOREIGN PATENT DOCUMENTS

| | | | |
|---|---|---|---|
| 6123955 | 9/1981 | Japan | 260/380 |
| 1572977 | 8/1980 | United Kingdom | 260/380 |

Primary Examiner—Glennon H. Hollrah
Assistant Examiner—Raymond Covington
Attorney, Agent, or Firm—Sprung Horn Kramer & Woods

[57] ABSTRACT

1-Amino-2-bromo-4-hydroxyanthraquinone is obtained in good yields and in an environmentally acceptable manner by bromination of 1-aminoanthraquinone in 2 to 5 times the quantity by weight of 80 to 98% strength sulphuric acid and using 1.1–1.5 mole of bromine under elevated pressure.

5 Claims, No Drawings

PROCESS FOR THE PREPARATION OF 1-AMINO-2-BROMO-4-HYDROXYANTHRAQUINONE

The invention relates to a process for the preparation of 1-amino-2-bromo-4-hydroxyanthraquinone by bromination of 1-aminoanthraquinone in concentrated sulphuric acid followed by hydroxylation in the presence of boric acid, no intermediate isolation of the bromination product being carried out.

"One-pot processes" of this type have already been described many times in the literature (see, for example, German patent specification Nos. 2,713,575 and 2,817,890). In these, as a rule the quantity of bromine is calculated such that 1-amino-2,4-dibromoanthraquinone is produced as nearly quantitatively as possible, and is then, without intermediate isolation, hydrolysed after addition of boric acid.

These methods of preparation, which no doubt represent a significant simplification in processing technology compared with the two-stage processes hitherto customary, nevertheless have the disadvantage that they are carried out with relatively large quantities of sulphuric acid and bromine and this not only considerably increases the costs of the preparation but also makes waste-water processing difficult.

It has now been found that the effects of these disadvantages can be markedly reduced when the bromination is carried out in 2 to 5 times the quantity by weight of 80 to 98% strength sulphuric acid ("initial concentration") and using 1.1–1.5 mole of bromine—in each case relative to 1-aminoanthraquinone—under elevated pressure.

Otherwise, both the bromination and the hydrolysis are carried out under customary conditions.

In this process, virtually the same yields and purities are obtained as in the processes of the state of the art which are carried out considerably more dilute or with higher quantities of bromine, and this has to be regarded as extremely surprising because the products obtained in concentrated media are normally of lower purity.

There is deliberate acceptance, in the use of less than equimolar quantities of bromine according to the invention, of the fact that, at the time hydrolysis is initiated, the bromination product contains 30–40% of 1-amino-2-bromoanthraquinone (in addition to the 2,4-dibromo derivative).

The fact that, nevertheless, a high-quality hydrolysis product is formed has likewise to be denoted surprising, since the teaching in the abovementioned patent specifications is that a large proportion of this monobromo derivative has an adverse effect on the purity of the hydrolysis product.

The bromination step is preferably carried out in 2.5–4 times the quantity of 90–96% strength sulphuric acid, at 60°–120° C., in particular at 70°–100° C., in an autoclave under an excess pressure of 0.5–5 bar, in particular 1–4 bar. The end of the bromination is reached when virtually no 1-aminoanthraquinone is any longer detectable in a sample which has been removed.

1.2–1.4 mole of bromine is preferably used.

The hydrolysis of the bromination mixture is carried out in the presence of boric acid (about 2–3 moles relative to 1-aminoanthraquinone), a sulphuric acid concentration of 95–110% being set up by addition of oleum. The temperatures are 100°–130° C.

All these conditions, as well as the work-up by discharge into water, belong to the state of the art.

Nevertheless, a special variation according to the invention takes the form of the boric acid being added at the start. The new one-pot process is even further simplified in this manner.

When the process is carried out in practice, the sulphuric acid is initially introduced and then the 1-aminoanthraquinone, boric acid and bromine are introduced at room temperature, and the pressure vessel is closed and heated to the desired reaction temperature. After the bromination, the pressure in the autoclave is released and it is charged with the necessary quantity of oleum. Then, without further industrial elaboration, the reaction is completed at customary temperatures.

EXAMPLE 1

9.0 kg of bromine are added to a mixture of 10.0 kg of 1-aminoanthraquinone (97%) and 15 l of 98% strength sulphuric acid at 50° C. in a pressure vessel. The reaction vessel is then tightly closed and the contents of the vessel are vigorously stirred at 70° C. for 1 hour, at 80° C. for 1 hour and finally at 90° C. for 2 hours.

The vessel is then cooled to 50° C. and the pressure is slowly released.

Without intermediate isolation, 5.5 kg of boric acid and 27 l of oleum (20%) are added consecutively and cautiously to the bromination mixture, the temperature being maintained at 50°–60° C. with cooling, before it is heated at 75° C. (1 hour) and then at 90° C. and 100° C. for 1 hour each. It is finally heated to 115° C. and stirred at this temperature for 6 hours, the bromine which is produced distilling out.

After cooling to 30°–40° C., excess bromine is removed in vacuo, and the reaction mixture is discharged onto 80 l of water. During this, the temperature rises to 90° C. The temperature is increased to 95° C. by blowing in steam. The mixture is allowed to stir at this temperature for 2 hours, and then the product is filtered off through a suction filter. After washing with hot water and drying, 12.4 kg—converted to 100% pure material—of 1-amino-2-bromo-4-hydroxyanthraquinone are obtained, which corresponds to a yield of 89.5%—the product contains less than 0.5% of 1-amino-4-hydroxyanthraquinone and about 1% each of 1-amino-2,4-dihydroxyanthraquinone and 1-amino-2,4-dibromoanthraquinone, together with traces of other bromo derivatives.

EXAMPLE 2

12 l each of sulphuric acid (96%) and oleum (20%) are initially introduced into a pressure vessel. With stirring, 8.25 kg of boric acid are introduced, it being possible for the temperature to rise to 60° C. After the boric acid has completely dissolved, 15 kg of 1-aminoanthraquinone are added to the solution at 40°–50° C. Stirring is continued for 1 hour and then 13.5 kg of bromine are cautiously run in.

The autoclave is now tightly closed and stirred at 70° C. for 1 hour, at 80° C. for 1 hour and at 90° C. for 2 hours, the pressure which is set up being 3.4–4 bar. After cooling and releasing the pressure, 34.5 l of oleum (20%) is allowed to run in slowly at 50°–65° C. The mixture is then heated gradually—as indicated in Example 1—to 115° C., and this temperature is maintained for 6 hours. Then working up is carried out as in Example 1.

Finally, 18.8 kg of 1-amino-2-bromo-4-hydroxyanthraquinone (converted to 100% pure material) are obtained, which corresponds to a yield of 90.4% of theory.

EXAMPLE 3

A stirring autoclave is charged consecutively with 40 kg of sulphuric acid (80% strength), 10 kg of 1-aminoanthraquinone (97% pure) and 3.4 l of bromine.

After closure of the pressure vessel, it is heated stepwise to 90° C. and maintained at this temperature for 2 hours. The vessel is allowed to cool to room temperature and the pressure is released.

Then 5.5 kg of boric acid are introduced and the mixture is vigorously stirred. Subsequently, with efficient cooling, 66 kg of oleum (65% strength) are cautiously allowed to run in. The internal temperature rises to 70° C. during this. The mixture is then heated stepwise to 115° C. and is stirred at this temperature for 6 hours. The reaction melt is then discharged onto 80 l of ice-water. The mixture thereby obtained is stirred at 95° C. for 2 hours and then discharged onto a filter press. After washing to neutrality and drying, 12.06 kg—converted to 100% pure material—(87% of theory) of a product consisting of 91.4% of 1-amino-2bromo -4-hydroxyanthraquinone and 2.3% of 1-amino-2, are obtained. The remainder was not identified on analysis.

EXAMPLE 4

The result obtained when only 2.7 l of bromine is used in place of 3.4 l of bromine is about as good as that in Example 3.

We claim:

1. Process for the preparation of 1-amino-2-bromo-4-hydroxyanthraquinone by bromination of 1-aminoanthraquinone in concentrated sulphuric acid and hydroxylation of the bromination product without intermediate isolation in the presence of boric acid under conditions which are otherwise customary, characterised in that the bromination is carried out in 2 to 5 times the quantity by weight of 80 to 98% pure sulphuric acid and using 1.1–1.5 mole of bromine—in each case relative to 1-aminoanthraquinone—under an excess pressure of 0.5–5 bar.

2. Process according to claim 1, characterised in that it is carried out in 2.5 to 4 times the quantity of sulphuric acid.

3. Process according to claim 1, characterised in that 1.2–1.4 mole of bromine is used.

4. Process according to claim 1, characterised in that it is carried out under an excess pressure of 1–5 bar.

5. Process according to claim 1, characterised in that the boric acid is added at the start of the bromination reaction.

* * * * *

UNITED STATES PATENT AND TRADEMARK OFFICE
CERTIFICATE OF CORRECTION

PATENT NO. : 4,741,867
DATED : May 3, 1988
INVENTOR(S) : Dittmer et al.

It is certified that error appears in the above-identified patent and that said Letters Patent is hereby corrected as shown below:

Col. 3, line 27     Insert --4-dibromoanthraquinone-- after "2,"

Signed and Sealed this

Thirteenth Day of December, 1988

Attest:

DONALD J. QUIGG

Attesting Officer      Commissioner of Patents and Trademarks